US012714360B2

(12) United States Patent
Kim

(10) Patent No.: US 12,714,360 B2
(45) Date of Patent: Aug. 25, 2026

(54) SYSTEM AND METHOD FOR IMPROVING SLEEP QUALITY

(71) Applicant: UNIVERSITY INDUSTRY FOUNDATION, YONSEI UNIVERSITY WONJU CAMPUS, Wonju-si (KR)

(72) Inventor: Tae Hui Kim, Wonju-si (KR)

(73) Assignee: UNIVERSITY INDUSTRY FOUNDATION, YONSEI UNIVERSITY WONJU CAMPUS, Wonju-si (KR)

( * ) Notice: Subject to any disclaimer, the term of this patent is extended or adjusted under 35 U.S.C. 154(b) by 245 days.

(21) Appl. No.: 18/512,490

(22) Filed: Nov. 17, 2023

(65) Prior Publication Data

US 2024/0156398 A1 May 16, 2024

Related U.S. Application Data

(63) Continuation of application No. PCT/KR2022/007104, filed on May 18, 2022.

(30) Foreign Application Priority Data

May 18, 2021 (KR) ........................ 10-2021-0064126
May 18, 2022 (KR) ........................ 10-2022-0060662

(51) Int. Cl.
*A61B 5/00* (2006.01)
*A61B 5/0205* (2006.01)
(Continued)

(52) U.S. Cl.
CPC .......... *A61B 5/4815* (2013.01); *A61B 5/0205* (2013.01); *A61B 5/1115* (2013.01);
(Continued)

(58) Field of Classification Search
None
See application file for complete search history.

(56) References Cited

U.S. PATENT DOCUMENTS

2005/0143617 A1* 6/2005 Auphan ............... A61B 5/4815 600/26
2020/0281521 A1 9/2020 Cail

FOREIGN PATENT DOCUMENTS

JP 2006-034966 A 2/2006
JP 5775868 B2 9/2015
(Continued)

OTHER PUBLICATIONS

Jeong, Jae-Heon et al.; "Development of AI Speaker with Active Interaction Customized for the Elderly"; The Journal of the Korea Institute of Electronic Communication Sciences; vol. 15, No. 6; Dec. 31, 2020, pp. 1223-1229.
(Continued)

*Primary Examiner* — Jay B Shah
(74) *Attorney, Agent, or Firm* — Bridgeway IP Law Group, PLLC; Jihun Kim

(57) ABSTRACT

The present disclosure relates to a system and method for improving sleep quality, and particularly, to a system and method for improving sleep quality that can induce correct sleep behavior of a user by measuring objective sleep quality in a wearless state and measuring and analyzing subjective sleep quality in a user-friendly manner. The system for improving sleep quality according to an embodiment of the present disclosure includes: a mattress configured to measure objective sleep quality information of a user in a wearless type; a behavior correction assistance device disposed at a predetermined distance from the mattress; and an AI speaker configured to integrate and analyze objective sleep quality information measured by the mattress and
(Continued)

subjective sleep quality information determined through Q&A with the user.

6 Claims, 4 Drawing Sheets

(51) Int. Cl.
*A61B 5/11* (2006.01)
*G16H 10/20* (2018.01)

(52) U.S. Cl.
CPC .......... *A61B 5/4368* (2013.01); *A61B 5/6891* (2013.01); *A61B 5/7405* (2013.01); *A61B 5/742* (2013.01); *G16H 10/20* (2018.01)

(56) References Cited

FOREIGN PATENT DOCUMENTS

| | | | |
|---|---|---|---|
| JP | 2020-022732 | A | 2/2020 |
| KR | 10-2013-0032891 | A | 4/2013 |
| KR | 10-1712281 | B1 | 3/2017 |
| KR | 10-2023524 | B1 | 9/2019 |

OTHER PUBLICATIONS

International Search Report issued in PCT/KR2022/007104; mailed Aug. 31, 2022.

* cited by examiner

SYSTEM AND METHOD FOR IMPROVING SLEEP QUALITY

TECHNICAL FIELD

The present disclosure relates to a system and method for improving sleep quality, and particularly, to a system and method for improving sleep quality that can induce correct sleep behavior of a user by measuring objective sleep quality in a wearless state and measuring and analyzing subjective sleep quality in a user-friendly manner.

BACKGROUND

Devices in the sleep industry market are focused only on accuracy or convenience in integrating various biological indexes and obtaining some kinds of information while overlooking recognition behavior errors that cause chronic insomnia. Such devices do not have clinical values for a high risk group for insomnia or objects who actually suffer from insomnia, and the value of merchantability and utility related to sleep may be deteriorated after the public's purchase for curiosity. Accordingly, it is required to integrate technological development while focusing on main clinical reasons for insomnia, that is, recognition errors related to sleep and inappropriate compensatory behavior for sleep.

The integration technique means striving for a sleep quality improvement effect by automatically measuring sleep recognition errors and compensatory behavior for sleep, proposes corrected behavior in accordance with the measured result, and measuring again sleep recognition errors and compensatory behavior for sleep with adaptation to the proposed behavior.

In relation to this, Korean Patent No. 10-2023524, which is a prior art document and relates to an insomnia treatment assistance device and an insomnia treatment assistance program, discloses a configuration that makes it possible to accurately measure sleepiness of a user by performing a sleepiness test at an appropriate time according to sleep efficiency showing the degree of improvement of insomnia. Further, Korean Patent No. 10-1712281, which relates to a calculating of sleep efficiency and managing sleep time in use with a wearable device and mobile application, discloses a configuration that enables accurate and timely treatment without a visit by calculating an average bed time (TB), calculating an average actual bed time (TS), determining whether there is a sleep disorder by calculating an average sleep efficiency (ES) on the basis of the average bed time and the average actual bed time, and providing a proposed bed time (TBp). Further, Japanese Patent Application Publication No. 2006-34966, which relates to an apparatus and method for evaluating and treating insomnia, discloses a configuration that makes a sleep behavior treatment plan on the basis of sleep pattern data and a behavior correction algorithm that creates stimulation of sleep induction behavior.

The related arts described above do not propose a configuration that generally measures and analyzes objective sleep quality and subjective sleep quality, and need to be modified in terms of a user-friendly individual-customized sleep guide function.

DETAILED DESCRIPTION

Technical Objectives

The present disclosure has been made in consideration of the matters described above and an objective of the present disclosure is to provide a system and method for improving sleep quality that helps a use have and maintain correct sleep behavior by developing IoT and artificial intelligence technologies for measuring correction behavior with recognition error measurement that actually helps improvement of sleep quality.

Summary

A system for improving sleep quality according to an embodiment of the present disclosure includes: a mattress configured to measure objective sleep quality information of a user in a wearless type; a behavior correction assistance device disposed at a predetermined distance from the mattress; and an AI speaker configured to integrate and analyze objective sleep quality information measured by the mattress and subjective sleep quality information determined through Q&A with the user.

In an embodiment, the mattress may include a weight/body pressure measurer configured to discriminate users by measuring weigh or body pressure of the user and an objective sleep measurer configured to discriminate sleep and arousal of the user, and the manner of discriminating sleep and arousal may use any one of brain waves, a heart rate, a respiratory rate, or movement.

In an embodiment, the mattress may further include a user information storage configured to store information measured by the weight/body pressure measurer to discriminate users on the mattress.

In an embodiment, the behavior correction assistance device may include a sensing unit configured to sense whether the user has sat thereon.

In an embodiment, behavior correction assistance device may include a body measurer configured to check, when the user sits thereon, whether the user is the same as the user who has lain on the mattress by measuring and comparing the weight of the user with those of the user who has lain on the mattress.

The method of improving sleep quality according to an embodiment of the present disclosure includes: (a) checking a user on a mattress; (b) measuring objective sleep quality of the user and transmitting the measured information to an AI speaker; (c) measuring subjective sleep quality of the user through the AI speaker; (d) measuring a recognition error and compensatory behavior by analyzing a match degree of the objective sleep quality information and the subjective sleep quality information; and (e) providing feedback information according to the result of measuring a recognition error and compensatory behavior.

Effectives

The system and method for improving sleep quality according to the present disclosure has the effect that it is possible to measure objective sleep quality in a wearless state without specific devices attached on the body of a user.

Further, the system and method for improving sleep quality according to the present disclosure has the effect that it is possible to perform an individual-customized guide function that prevents insomnia and promotes correction by measuring compensatory behavior with recognition of sleep and analyzing a pattern.

Further, the system and method for improving sleep quality according to the present disclosure has the effect that it is possible to replace a sleep diary that is used insomnia recognition behavior treatment in a clinic.

Further, the system and method for improving sleep quality according to the present disclosure has the effect of being able to be easily used by the elderly who has insomnia in many cases and being able to contribute to mental stability of the elderly.

Further, the system and method for improving sleep quality according to the present disclosure has the effect that it is expected to construct a healthy lifestyle for preventing depression and dementia by reducing insomnia and it is possible to give a mutual positive influence on the study of smart devices related to feeling and recognition function that has been conducted so far without excluding the influence by sleep.

BRIEF DESCRIPTION OF THE DRAWINGS

The above and other objectives, features and other advantages of the present disclosure will be more clearly understood from the following detailed description when taken in conjunction with the accompanying drawings, in which.

BEST MODE

Figure 1:
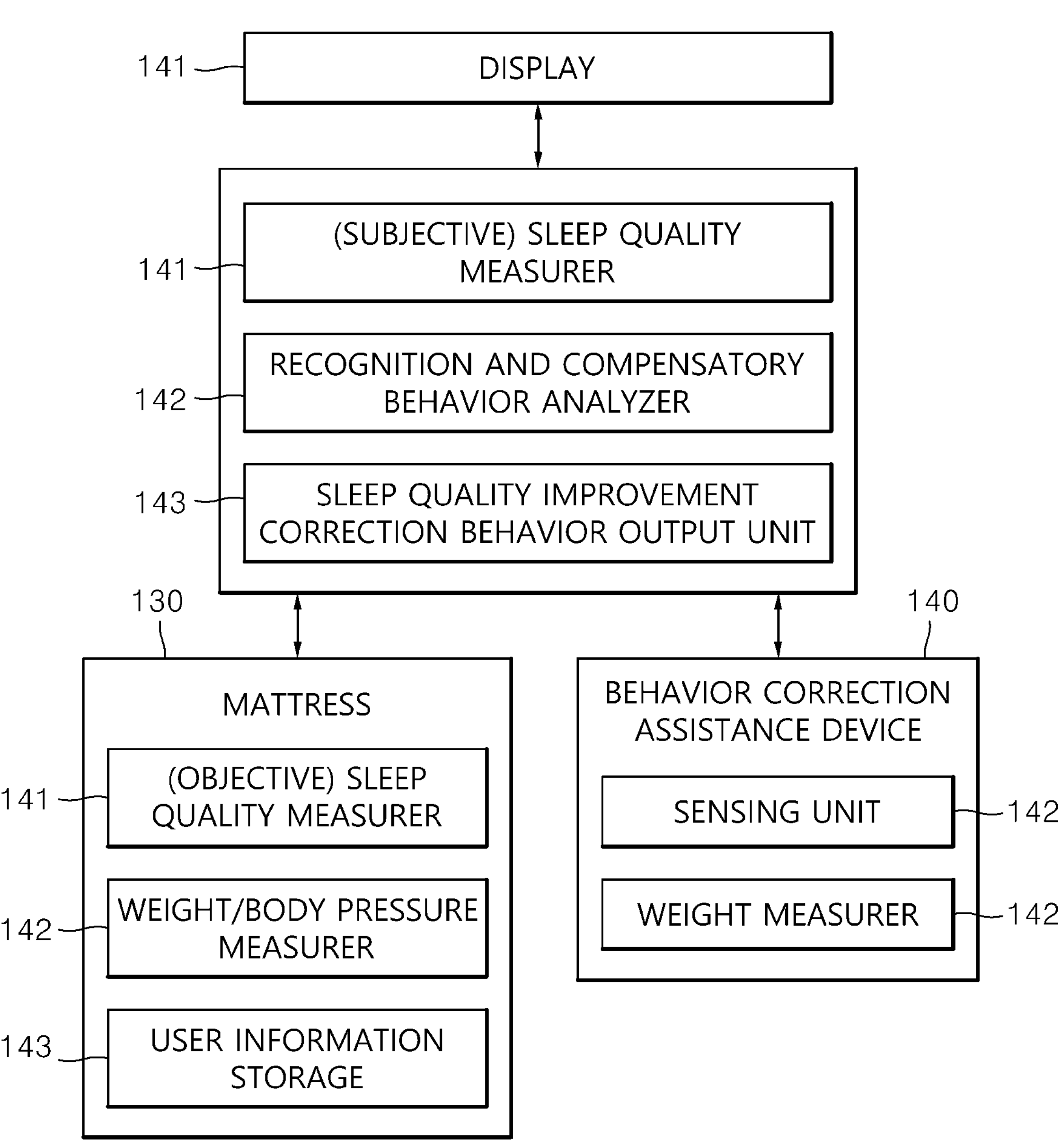
FIG. 1 is a block diagram showing a system for improving sleep quality according to an embodiment of the present disclosure.

Hereinafter, embodiments of the present disclosure are described in detail with reference to exemplary drawings. It should be noted that when components are given reference numerals in the drawings, the same components are given the same reference numerals even if they are shown in different drawings. In describing the present disclosure, well-known functions or constructions will not be described in detail since they may unnecessarily obscure the understanding of the present disclosure.

FIG. 1 is a block diagram showing a system for improving sleep quality according to an embodiment of the present disclosure.

Referring to FIG. 1, a system 10 for improving sleep quality of the present disclosure includes a mattress 100, a behavior correction assistance device 200, and an Artificial Intelligence (AI) speaker 300, and selectively, further includes a display 400.

Insomnia relates to discord between objective sleep quality (OSQ) and subjective sleep quality (SSQ), that is, a recognition error, and is characterized by compensatory behavior that increases a time of staying awake on a bed. It is possible to prevent insomnia from becoming chronic and reduce worries and anxiety about sleep only when reducing such compensatory behavior.

The system 10 for improving sleep quality of the present disclosure immediately and friendly talks about whether a user had a good sleep, etc. with the user when the user gets up, checks sleep quality, a recognition error, and compensatory behavior by integrating the talk with information measured from the mattress 100, and provides feedback according to the result, thereby helping prevent or correct insomnia.

Objective sleep quality (OSQ) information is measured in a wearable type such as an actiwatch or is measured through polysomnography at hospital and the mattress 100 of the present disclosure can measure it in a wearless type at home, so it is possible to make it easy to measure objective sleep quality information and measure compensatory behavior that is a factor making insomnia worse.

The mattress 100 can measure sleep or arousal when a user is lying, and measures a time for which a user is lying on the mattress by sensing the weight of the user.

To this end, the mattress 100 can include an objective sleep measurer 110 and a weight/body pressure measurer 120.

The objective sleep measurer 110 of the mattress can obtain objective sleep quality (OSQ) information such as Sleep onset latency (SoL), Sleep duration or Total Sleep Time (TST), and Wake After Sleep Onset (WASO) by measuring sleep and arousal and the weight/body pressure measurer 120 obtains Time in Bed (TIB) such that it is possible to analyze Sleep Efficiency (SE) that is objective sleep quality information.

The objective sleep measurer 110 can use any one of brain waves, a heart rate, a respiratory rate, or movement. An EEG machine that is supposed to be positioned at the area where the user's head is placed may be used for brain waves, a piezo sensor, infrared photoplethysmography (PPG), photoplethysmography, or the like may be used for a heart rate or a respiratory rate, and an accelerator, etc. may be used for movement. The sleep measurer may include sleep structure measurement such as REM and slow wave sleep, but consistently discriminates a sleep state including all of slow wave sleep, REM, etc. and an arousal state that is not a sleep state.

The weight/body pressure measurer 120 discriminates users on the mattress 100 by measuring the weight or body pressure of the users and provides information about a time in bed and a wake-up time of a user on the mattress 100 such that it is possible to check the compensatory behavior for sleep of the user.

The user information storage 130 stores weight or body pressure information measured by the weight/body pressure measurer 120 and discriminates users. Many different users may lie on the mattress 100 and information measured by the weight/body pressure measurer 120 is stored in the user information storage 130, so it is possible to discriminate users on the mattress 100.

The subjective sleep quality (SSQ) information is determined through a sleep diary written by an individual, and education and repeated performance are required to correctly make a sleep diary. The elderly who has insomnia has difficulty in making a sleep diary due to various reasons, so it is difficult to smoothly provide recognition behavior treatment for them.

The AI speaker 300 of the present disclosure may include a subjective sleep measurer 310, a recognition error and compensatory behavior analyzer 320, and a sleep quality improvement correction behavior output unit 330. The subjective sleep measurer 310 is equipped with software composed appropriate content in a friendly conversation type and can easily measure subjective sleep quality instead of a sleep diary for determining subjective sleep quality, and particularly, is easy to be applied to the elderly.

The recognition error and compensatory behavior analyzer 320 analyzes variation of an error about whether there is a recognition error on the basis of the match degree and the degree of difference of measurement values such as a time in bed measured by the objective sleep measurer 110 of the mattress and the subjective sleep measurer 310 of the AI speaker. The recognition error and compensatory behavior analyzer 320 calculates sleep efficiency (SE) information corresponding to the objective sleep quality and analyzes whether there is compensatory behavior for sleep using the total sleep time (TST) obtained by the objective sleep measurer 110 and the time in bed (TIB) obtained by the weight/body pressure measurer 120. The sleep quality improvement correction behavior output unit 330 proposes a user with sleep time hours, that is, time to go to bed by applying an algorithm that guides compensatory behavior for sleep and a sleep efficiency increase.

The AI speaker of the present disclosure can guide a user to be positioned at the behavior correction assistance device before going to bed or to get out of the bed and then be positioned at the behavior correction assistance device after going to bed in accordance with an algorithm that analyzes a recognition error and compensator behavior, analyzes whether they are and their patterns, and proposes a behavior strategy for reducing the time of compensatory behavior by integrating the information measured by the subjective sleep measurer 310, objective sleep measurer 110, and the weight/body pressure measurer 120.

There are various reasons that cause sleep problems including a sleep environment problem and obstructive sleep apnea syndrome, but the mechanism that fixes and maintains chronic insomnia is because individual dysfunctional thinking and maladaptive behavior, that is, recognition behavior errors act to sleep.

Devices in the sleep industry market are focused only on accuracy (problem diagnosis) and convenience in integrating various items of biological index information related to insomnia while overlooking recognition behavior errors, but when objects who have a danger of insomnia or actually suffer from insomnia are made have an interest in objective data and environment control related to sleep, anxiety about sleep is increased and maladaptive compensatory behavior is promoted, so insomnia may become worse. Accordingly, these devices have limitation that it is difficult to expect a clinical value.

The system 10 for improving sleep quality of the present disclosure is a practical system that can improve recognition behavior errors, and measures recognition and behavior for optimal sleep by applying IoT and artificial intelligence technologies to be able to provide an individual-customized service, and promotes correction of behavior.

The behavior correction assistance device 200 is used to correct behavior such that a user stays at a place separate from the mattress 100 when he/she is awake. The behavior correction assistance device 200 is disposed at a position spaced a predetermined distance apart from the mattress 100, and though not specifically limited, may be a product on which a user can sit such as a sofa or a cushion. The behavior correction assistance device 200 includes a sensing unit 210, so it can sense whether a user has sat thereon.

In another embodiment of the present disclosure, the behavior correction assistance device 200 includes a weight measurer 220, so when a user sits thereon, it can check whether the user is the same as the user who has lain on the mattress 100 by measuring the weight of the user and comparing their weights. A transceiver may be attached to each of the mattress 100 and the behavior correction assistance device 200 to transmit/receive weight information of a user.

Information about whether a user uses the behavior correction assistance device 200 can be used for behavior adaptivity or behavior variation and insomnia improvement measurement of the user. Improvement of insomnia is determined using an objective or subjective difference or a match degree of a sleep time value and sleep efficiency, and the values may be, for example, 30 minutes or less and 85% or more.

Information about whether a user uses the behavior correction assistance device 200 can be used for behavior adaptivity or behavior variation measurement.

The AI speaker 300 integrates and analyzes information that is transmitted from the mattress 100 and the behavior correction assistance device 200. The AI speaker 300 obtains information about sleep of a user who waked up to analyze subjective sleep quality (SSQ) and estimates a match degree by comparing the objective total sleep time (TST) and objective sleep efficiency (SE) measured from the mattress 100 and the subjective total sleep time (TST) and subjective sleep efficiency (SE) measure from the AI speaker 300.

In this case, the sleep efficiency means the time for which a user actually slept when the user was lying on bed. That is, sleep efficiency (%)=(actual total sleep time (TST)/time in bed (TIB))×100. The higher the sleep efficiency, the higher the efficiency may be considered, and appropriate sleep efficiency is at least 85%. On the contrary, when sleep efficiency is 85% or lower, a user may feel severely tiered next day. This is because it means that a user tried to sleep, but he/she has not slept as much as his/her effort and tossed and turned for the time.

The AI speaker 300 determines whether there is a recognition error and compensatory behavior for sleep using the match degree of objective sleep efficiency and subjective sleep efficiency and then informs the user of appropriate behavior on that day, that is, time to go to bed and behavior when waking up while sleeping. The AI speaker 300 can inform a user of behavior information using a voice through the speaker and may output the information as visualized information on the display 400 wirelessly connected to the AI speaker 300.

The display 400 is a device that visualizes and shows information that is transmitted from the AI speaker 300. The display 400, though not specifically limited, may be a TV, a computer monitor, etc. When the AI speaker 300 provides feedback information about behavior of a user, a visual support matter through the display 400 may be used other than the voice support manner through a speaker, which can increase convenience and recognition for the user. In particular, it can be used as a system having a friendly property for the elderly who has a high possibility of insomnia.

The AI speaker 300 provides feedback information about behavior of a user and then informs the user that the user practiced the behavior in accordance with the provided information next day. The AI speaker 300 can transmit motive enhancement education data to the display 400 in accordance with the motive level of behavior correction.

In an embodiment of the present disclosure, the AI speaker 300 and the display 400 may be integrated. In another embodiment of the present disclosure, the AI speaker 300 and the behavior correction assistance device 200 may be integrated. When they are integrated, it is possible to increase utility of space and convenience in management by reducing the number of physical parts constituting the system 10 for improve sleep quality.

Figure 2:
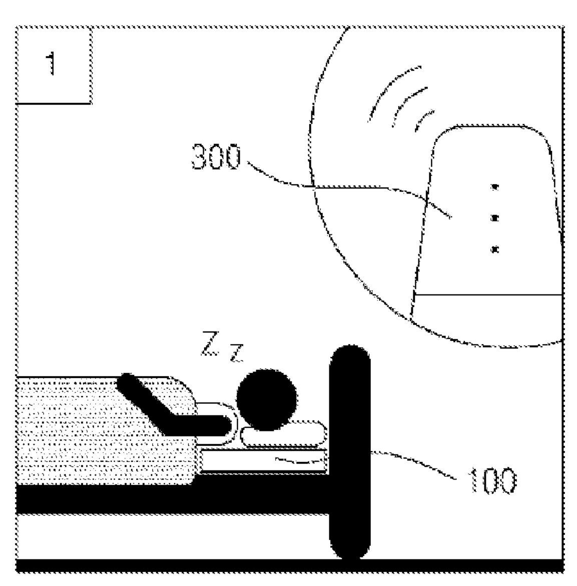
FIG. 2 is a diagram exemplarity showing the operation of the system for improving sleep quality according to an embodiment of the present disclosure.
Figure 2:
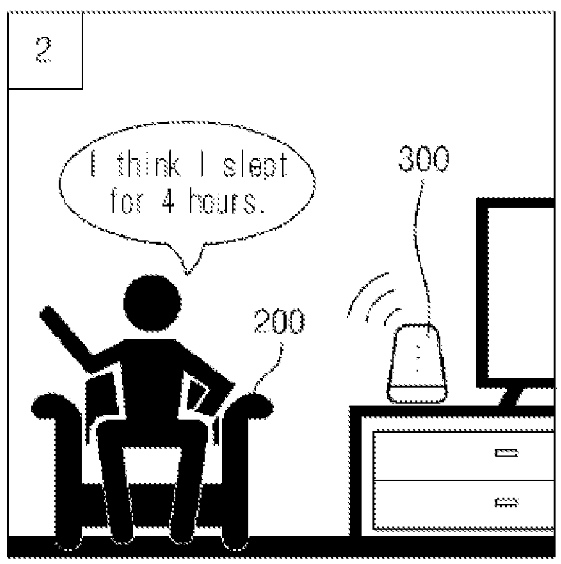
Figure 2:
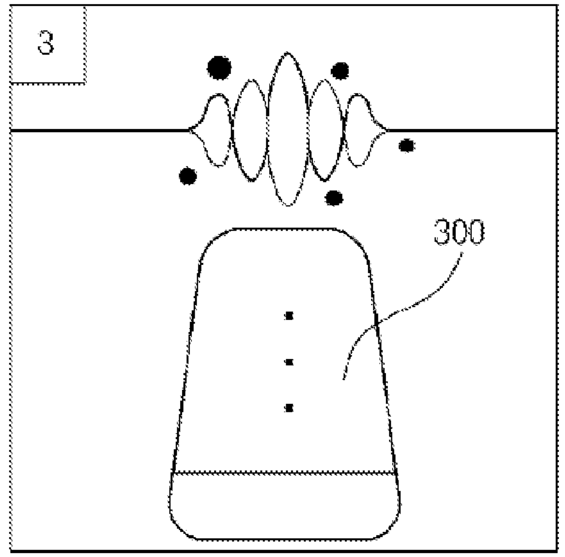
Figure 2:
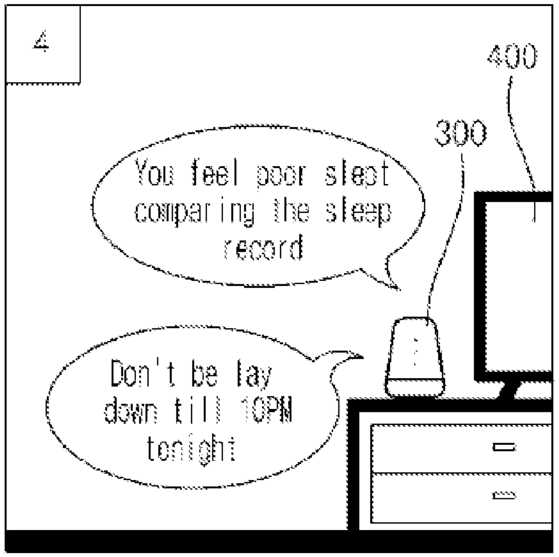

FIG. 2 is a diagram exemplarity showing the operation of the system for improving sleep quality according to an embodiment of the present disclosure.

In (1) of FIG. 2, a value measured at the mattress 100 while a user sleeps is transmitted to the AI speaker 300. The user information measured at the mattress 100 is weight/body pressure information, information about sleep/arousal, etc.

In (2) of FIG. 2, when a user wakes up, the user moves out of the mattress 100, sits on the behavior correction assistance device 200, and talks with the AI speaker 300.

In this case, the user can ask and respond about the sleep during the last night in accordance with a predetermined scenario program. For example, it is possible to say like "I think I slept for 4 hours".

In (3) of FIG. 2, the AI speaker 300 calculates objective sleep efficiency and subjective sleep efficiency from objective sleep quality (OSQ) information transmitted from the mattress 100 and subjective sleep quality (SSQ) information determined through conversation with the user and analyzes the match degree of them, a recognition error, etc.

In (4) of FIG. 2, the AI speaker 300 provides feedback information to the user on the basis of the analyzed information and transmits behavior for better sleep quality in a detailed and user-20 friendly manner.

For example, it is possible to aurally and visually transmit "You feel poor slept comparing the sleep record" and "Don't be lay down till 10 PM tonight" through the AI speaker or a monitor.

Figure 3:
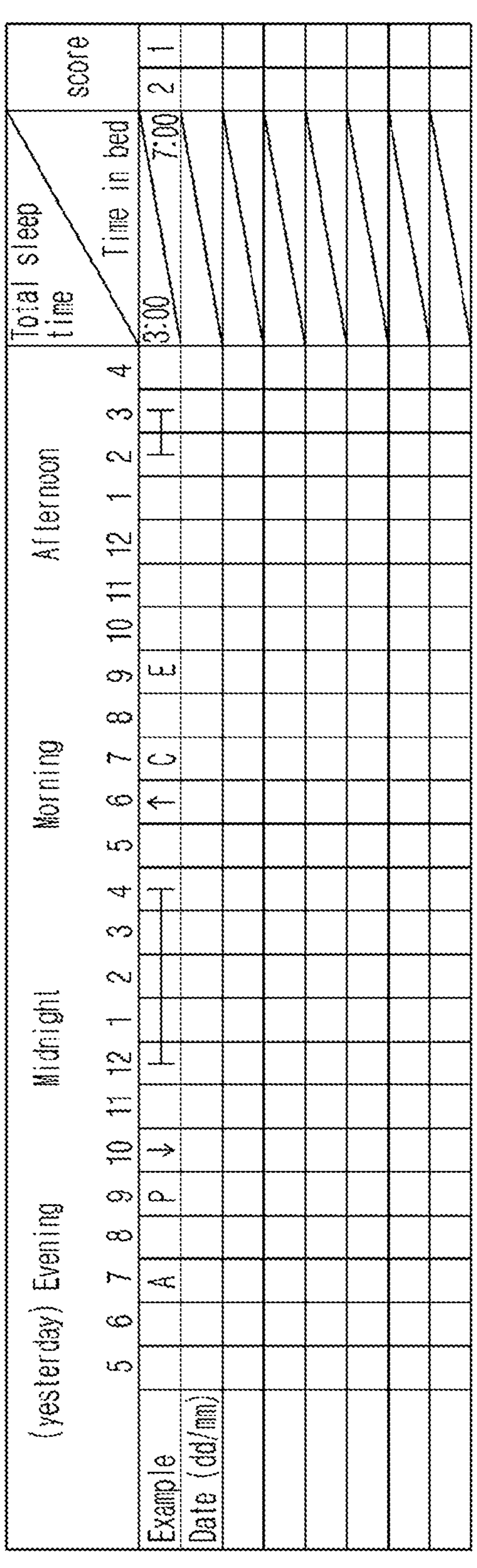
FIG. 3 shows an example of a sleep diary for determining subjective sleep quality.

FIG. 3 shows an example of a sleep diary for determining subjective sleep quality.

Recognition behavior treatment is performed to improve sleep efficiency of a user who suffers from a sleep disorder, the user is made perceive his/her compensatory behavior for sleep by making him/her write a sleep diary during the period of the recognition behavior treatment, and individual behavior is prescribed for increasing sleep efficiency over 85%.

The main content of the sleep diary is showing sleep-relevant information such as the time of going to bed, the time of getting out of bed, the time of falling asleep, the time of waking up, the time of taking a medicine or drinking, an exercise time, a nap time, and the degree of feeling well after sleeping. Users write values (subjective sleep quality information) that they perceive on their memories rather than writing the accurate time using a clock for corresponding sleep-relevant information in a sleep diary.

For example, referring to the figures, brief personal information, a user is supposed to mark "↓" for the time of turning off the lights or lying down to sleep in a day, mark "↑" for the time of turning on the lights or getting out of bed in a day, mark "1 -- ----- 1" when he/she did not sleep including a nap in a day, mark "A" for the period of drinking alcohol, mark "C" for the time of having a coffee, mark "P" for the time of taking a pill for sleep, mark "E" for the time of exercising, and record how long he/she lay down and slept during the night.

Further, Score 1 shows the degree of satisfaction at sleep last night from 1 to 5 and is configured to be able to estimate the degree with 1 for very bad, 2 for bad, 3 for medium, 4 for good, and 5 for very good.

Score 2 shows the degree of feeling well in the morning after sleeping is configured to be able to estimate the degree with 1 for very bad, 2 for bad, 3 for medium, 4 for good, and 5 for very good.

When a use has insomnia, the objective sleep quality or sleep efficiency that is determined through a sleep diary does not coincide with the subjective sleep quality or sleep efficiency such as an actiwatch or polysomnography, and even though the user objectively had a sleep for 5 or more hours, he/she does not feel like that, so he/she may be attached to medicine in some cases.

The AI speaker 300 of the present disclosure can obtain subjective sleep quality information instead of the sleep diary of the related art described above. That is, the AI speaker 300 of the present disclosure asks a user sleep-relevant information such as the time of lying on the mattress 100, the time of getting out of the mattress 100, the time of falling a sleep, the time of waking up, the time of taking a medicine or drinking, an exercise time, a nap time, and the degree of feeling well after sleeping, and obtains and analyzes answers from the user, thereby being able to determine the subjective sleep quality information of the user. To this end, sleep-relevant questions for a user may be programmed in the AI speaker 300 in advance to measure the subjective sleep quality of the user.

The system 10 for improving sleep quality of the present disclosure can help healthy sleep habits by measuring sleep behavior with recognition of sleep and providing feedback, can prevent insomnia from becoming worse, and reduce cases in which it is required to visit medical facilities or sleep specialists.

The system 10 for improving sleep quality can achieve actual sleep improvement effect, particularly, for the elderly. It is very difficult for the elderly to make a writing-type sleep diary that is currently clinically used, and more explanation and repetition are required for the elderly to smoothly make such as sleep diary in comparison to general adults. However, since the AI speaker 300 of the present disclosure can obtain information in a Q&A type through a voice, it is possible to reduce the difficulty that the elderly feels in the related art and this manner is useful in connection with clinic latter.

The system 10 for improving sleep quality obtains objective sleep quality information in the type that a user lies on a mattress without wearing a wearable device, the system is convenient to use.

Figure 4:
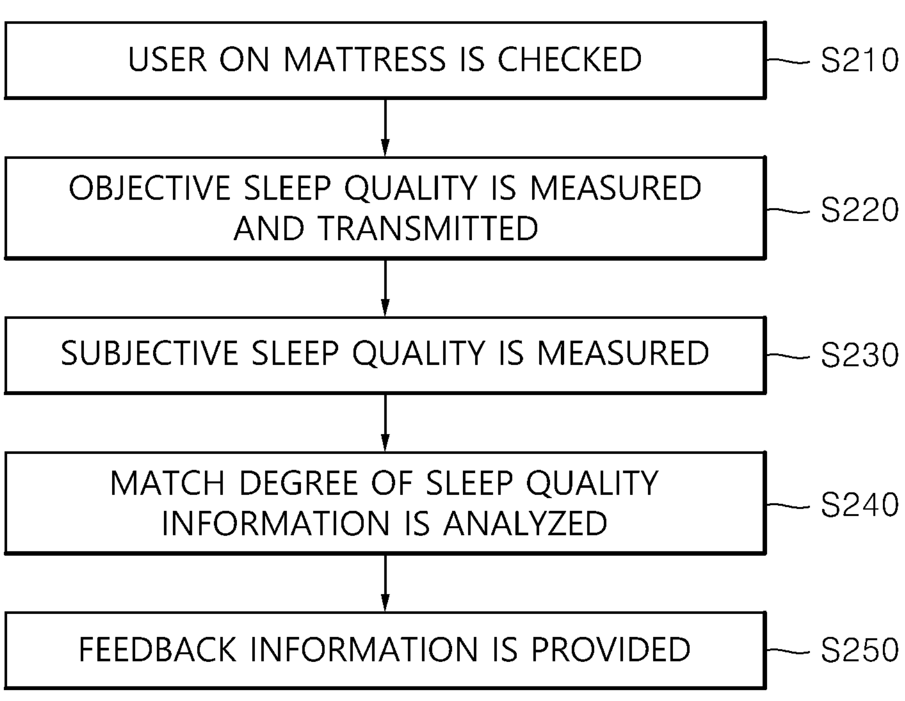
FIG. 4 is a flowchart showing a method of improving sleep quality according to an embodiment of the present disclosure.

FIG. 4 is a flowchart showing a method of improving sleep quality according to an embodiment of the present disclosure.

Referring to FIG. 4, first, a user on the mattress 100 is checked, and to this end, the weight/body pressure measurer 120 can measure the weight of the body pressure of the user. Since many users may lie on the mattress 100, information measured by the weight/body pressure measurer 120 is stored in the user information storage 130. Accordingly, when someone lies on the mattress 100 later, it is possible to discriminate the user using the stored weight or body pressure information.

Next, the mattress 100 measures the objective sleep quality of the user and transmits the measured information to the AI speaker (S220). In this case, the objective sleep quality may include one or more items of information of a total sleep time, sleep onset latency, an arousal time, or sleep efficiency.

Next, the AI speaker 300 measures the subjective sleep quality of the user (S230).

In this case, the subjective sleep quality may include one or more items of information of the time of lying on the mattress, the time of getting out of the mattress, the time of falling asleep, the time of waking up, the time of taking a medicine or drinking, an exercise time, a nap time, for the degree of feeling well after sleeping. Sleep-relevant questions for users composed of appropriate content in a friendly conversation type to measure subjective sleep quality of users may be programmed in advance in the AI speaker 300 of the present disclosure.

In an embodiment of the present disclosure, measurement of subjective sleep quality by the AI speaker 300 may be performed at the behavior correction assistance device 200 spatially spaced apart from the mattress 100. By inducing a user to get out of the mattress 100 and sit on the behavior correction assistance device 200 when the user wakes up, it is possible to correct wrong compensatory behavior for sleep of the user, etc.

Next, the AI speaker 300 measures a sleep recognition error and compensatory behavior of the user by analyzing the match degree of the objective sleep quality information transmitted from the mattress 100 and the subjective sleep quality information obtained through Q&A with the user (S240).

Next, the AI speaker 300 can provide the user with feedback information according to the result of measuring the recognition error and compensatory behavior of the user (S250). To this end, it is possible to provide feedback information through the voice of the AI speaker 300 or provide feedback information through the voice of the AI speaker 300 and visualized information of the display 400.

Further, the embodiments described above can be achieved by hardware components, software components, and/or a combination of hardware components and software components. For example, the system, method, and components described in the embodiments by one or more common computers or computers for specific purposes, such as a processor, a controller, an ALU (arithmetic logic unit), a digital signal processor, a microcomputer, an FPGA (field programmable gate array), a PLU (programmable logic unit), a microprocessor, or any devices that can execute instructions and give responses. A processing device can perform an operating system (OS) and one or more software applications that are executed on the OS. Further, the processing device can access, store, operate, process, and create data in response to execution of software. For the convenience of understanding, one processing device may be used, but those skilled in the art can understand that the processing device may include a plurality of processing elements and/or a plurality of types of processing elements. For example, the processing device may include a plurality of processors or, one processor and one controller. Further, other processing configurations such as parallel processors are possible.

Software can include computer programs, codes, instructions, or a combination of one or more of them, and a processing device may be configured to operate in a desired way or processing devices may be configured individually or collectively. Software and/or data may be analyzed by processing devices or may be permanently or temporarily embodied on any types of machines, components, physical devices, virtual equipment, computer storage media or devices, or signal waves to be transmitted. Software may be distributed to computer systems connected through a network and stored or executed in the distributed way. Software or data may be stored in one or more computer-readable recording media.

The method according to an embodiment may be implemented in a program that can be executed by various computers and may be recorded on computer-readable media. The computer-readable media may include program commands, data files, and data structures individually or in combinations thereof. The program commands that are recorded on the media may be those specifically designed and configured for the present invention or may be those available and known to those engaged in computer software in the art. The computer-readable recording media include magnetic media such as hard disks, floppy disks, and magnetic media such as a magnetic tape, optical media such as CD-ROMs and DVDs, magneto-optical media such as floptical disks, and hardware devices specifically configured to store and execute program commands, such as ROM, RAM, and flash memory. Examples of the program instructions include not only machine language compiled by a compiler, but also high-level language codes that can be executed by a computer using an interpreter. The hardware device may be configured to operate as one or more software modules to perform the operation of the present invention, and vice versa.

Although the present disclosure was described above in detail preferred embodiment, the present disclosure is not limited to the embodiments described above and it is apparent to those skilled in the art that the spirit of the present disclosure reaches the range in which the present disclosure can be changed and modified in various ways without departing from the scope of the present disclosure defined in the following claims.

Industrial Applicability

The present disclosure has competence that can manage sleep behavior, assist a user to actually improve his/her sleep quality, and provide new-concept sleep industry device and service by using a sleep product that helps healthy habits by measuring sleep behavior with recognition of sleep and providing feedback to be able to prevent insomnia from becoming worse and reduce cases of visiting medical facilities of sleep specialists.

What is claimed is:

1. A method of a system for improving sleep quality, the system comprising a mattress and a behavior correction assistance device configured to collect and analyze sleep quality information of a user of the system and generate a sleep behavior correction instruction catered to the user, and the method comprising:

(a) measuring a first weight of the user on the mattress via a first weight measurer installed in the mattress;

(b) measuring an objective sleep quality information of the user via sensors installed in the mattress and transmitting the measured objective sleep quality information to an AI speaker of the behavior correction assistance device;

(c) detecting that the user is seated on the behavior correction assistance device in a form of a sofa or a cushion physically spaced apparat from the mattress and measuring a second weight of the user via a second weight measurer installed in the behavior correction assistance device;

(d) verifying that the user seated on the behavior correction assistance device is identical to the user on the mattress by comparing the first weight and the second weight;

(e) measuring a subjective sleep quality information of the user through audible interaction with the AI speaker while the user is seated on the behavior correction assistance device;

(f) measuring a recognition error and a compensatory behavior by analyzing a match degree between the objective sleep quality information and the subjective sleep quality information, wherein the recognition error is a discord between the objective sleep quality information and the subjective sleep quality information and the recognition error is characterized by the compensatory behavior; and (g) generating the sleep behavior correction instruction catered to the user via the AI speaker based on the recognition error and the compensatory behavior.

2. The method of claim 1, wherein the measuring of the first weight in the step (a) further comprises detecting a presence of the user on the mattress.

3. The method of claim 1, wherein the objective sleep quality information includes one or more items of information of a total sleep time, sleep onset latency, an arousal time, or sleep 10 efficiency.

4. The method of claim 1, wherein the subjective sleep quality information includes any one or more items of information of a time of lying on the mattress, a time of getting out of the mattress, a time of falling asleep, a time of waking up, a time of taking a medicine or drinking, an exercise time, a nap time, and a degree of feeling well after sleeping.

5. The method of claim 1, wherein sleep-relevant questions for the user are programmed in advance in the AI speaker to measure the subjective sleep quality information of the user.

6. The method of claim 1, wherein the generating the sleep behavior correction instruction of the step (g) is further made through a a display integrated with the AI speaker.

* * * * *